United States Patent [19]
Morrison et al.

[11] Patent Number: 5,891,145
[45] Date of Patent: Apr. 6, 1999

[54] MULTI-AXIAL SCREW

[75] Inventors: Matthew Morrison; Michael C. Sherman; Troy Drewry, all of Memphis, Tenn.

[73] Assignee: SDGI Holdings, Inc., Wilmington, Del.

[21] Appl. No.: 892,582

[22] Filed: Jul. 14, 1997

[51] Int. Cl.$^6$ .................................................. A61B 17/70
[52] U.S. Cl. ................................ 606/61; 606/73; 606/60
[58] Field of Search ................................ 606/60, 61, 72, 606/73, 69, 70, 71

[56] References Cited

U.S. PATENT DOCUMENTS

| | | | |
|---|---|---|---|
| 4,946,458 | 8/1990 | Harms et al. | 606/61 |
| 5,005,562 | 4/1991 | Cotrel | 128/69 |
| 5,084,048 | 1/1992 | Jacob et al. | 606/61 |
| 5,207,678 | 5/1993 | Harms et al. | 606/61 |
| 5,261,909 | 11/1993 | Sutterlin et al. | 606/61 |
| 5,312,404 | 5/1994 | Asher et al. | 606/61 |
| 5,443,467 | 8/1995 | Biederman et al. | 606/65 |
| 5,466,237 | 11/1995 | Byrd, III et al. | 606/61 |
| 5,476,464 | 12/1995 | Metz-Stavenhagen et al. | 606/61 |
| 5,501,684 | 3/1996 | Schlapfer et al. | 606/73 |
| 5,520,690 | 5/1996 | Errico et al. | 606/61 |
| 5,531,746 | 7/1996 | Errico et al. | 606/61 |
| 5,549,608 | 8/1996 | Errico et al. | 606/61 |
| 5,554,157 | 9/1996 | Errico et al. | 606/61 |
| 5,575,792 | 11/1996 | Errico et al. | 606/61 |
| 5,578,033 | 11/1996 | Errico et al. | 606/61 |
| 5,584,834 | 12/1996 | Errico et al. | 606/61 |
| 5,586,984 | 12/1996 | Errico et al. | 606/61 |
| 5,607,426 | 3/1997 | Ralph et al. | 606/61 |
| 5,609,593 | 3/1997 | Errico et al. | 606/61 |
| 5,609,594 | 3/1997 | Errico et al. | 606/61 |

*Primary Examiner*—Michael Buiz
*Assistant Examiner*—David O. Reip
*Attorney, Agent, or Firm*—Woodard, Emhardt, Naughton, Moriarty & McNett

[57] ABSTRACT

A spinal fixation assembly is provided that includes a bone engaging fastener and an elongated member, such as a spinal rod. The fixation assembly is a multi-axial assembly that permits fixation of the bone engaging fastener to the spinal rod at any of a continuous range of angles relative to the rod in three-dimensional space. The fixation assembly includes a receiver member having a bore therethrough, the walls of which are tapered near the bottom, and a channel communicating with the bore and having an upper opening at the top of the receiver member for insertion of a spinal rod. Also included are an outer wedge member and an inner wedge member, both of which have generally the shape of a washer and a bore therethrough. In each wedge member, the respective bore is not parallel to the central axis of the respective wedge member. Additionally, the outside surfaces of the wedge members may be tapered, and the respective bores may be tapered, so as to self-lock when seated and tightened. The bone engaging fastener fits within the bore of the inner wedge member, which in turn fits within the bore of the outer wedge member, which in turn fits within the tapered sides of the receiver member. When the desired position of the bone engaging fastener in three-dimensional space is attained, the components are seated to achieve a tight friction fit.

21 Claims, 6 Drawing Sheets

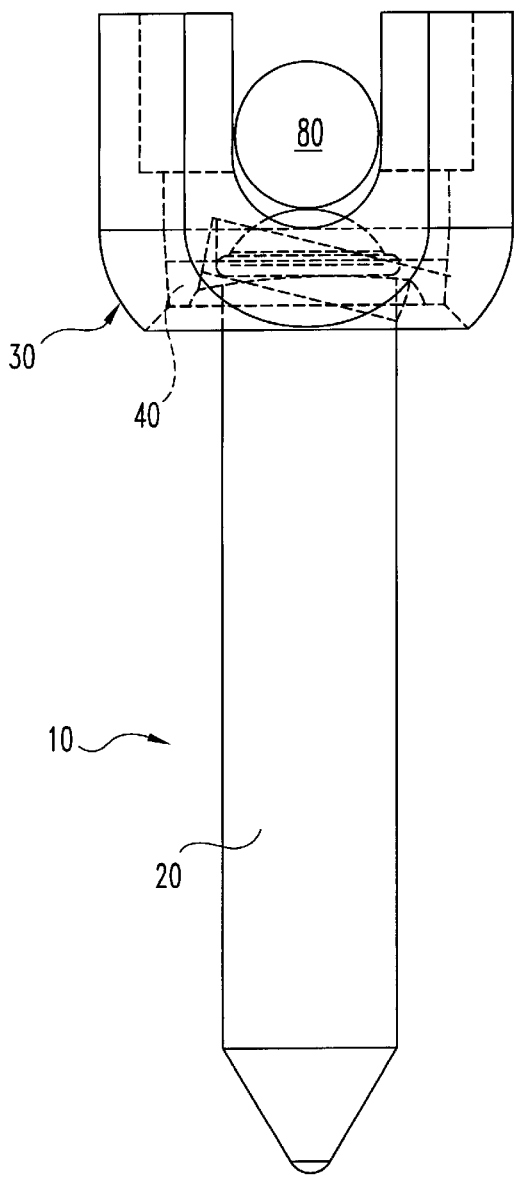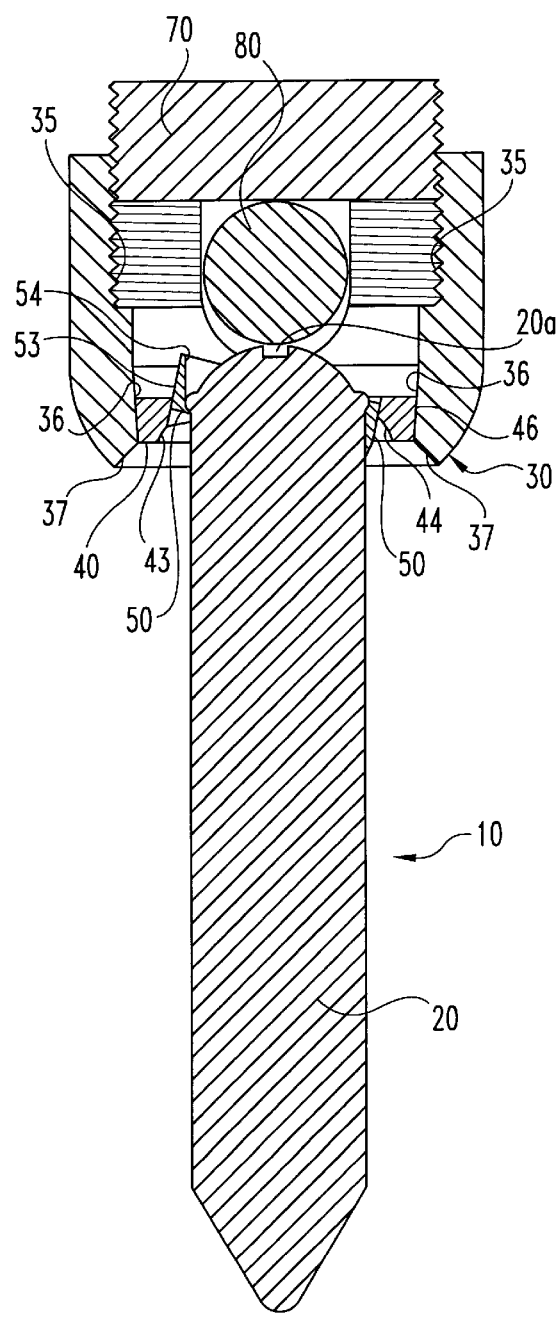
Fig. 1
Fig. 2

MULTI-AXIAL SCREW

BACKGROUND OF THE INVENTION

The present invention concerns a bone fixation assembly, particularly useful for engagement in the vertebrae. In particular, the invention provides a bone screw assembly that is capable of a continuous range of three-dimensional angular orientations with respect to an elongated member extending along the spine.

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another prevalent fixation element is a spinal screw which can be threaded into various aspects of the vertebral bone.

In one typical procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to these plurality of bone screws to apply corrective and stabilizing forces to the spine.

One example of a rod-type spinal fixation system is the TSRH® Spinal System sold by Danek Medical, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allowed the surgeon to easily engage a bent spinal rod to each of the fixation elements for final tightening.

Another rod-type fixation system is the Cotrel-Dubosset/CD Spinal System sold by Sofamor Danek Group, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screw with this "open-back" configuration. Details of this technology can be found in U.S. Pat. No. 5,005,562 to Dr. Cotrel. One benefit of this feature of the CD® System is that the fixation element is positioned directly beneath the elongated rod. This helps reduce the overall bulkiness of the implant construct and minimizes the trauma to surrounding tissue.

On the other hand, these fixation elements of the CD® System are capable only of pivoting about the spinal rod to achieve variable angular positions relative to the rod. While this limited range of relative angular positioning is acceptable for many spinal pathologies, many other cases require more creative orientation of a bone screw, for instance, relative to a spinal rod. Certain aspects of this problem are addressed by the variable angle screw of the TSRH® System, as discussed in the '909 Patent. However, there is a need for a bone screw that is capable of angular orientation in multiple planes relative to the spinal rod. Preferably, the bone screw is capable of various three-dimensional orientations with respect to the spinal rod. Screws of this type have been referred to as multi-axial or multi-axial bone screws.

Others have approached the solution to this problem with various multi-axial screw designs. For example, in U.S. Pat. No. 5,466,237 to Byrd et al., a bone screw is described which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

In another apprih shown in U.S. Pat. No. 4,946,458 to Harms et al., a spherical headed bone screw is supported within separate halves of a receiver member. The bottom of the halves are held together by a retaining ring. The top of the receiver halves are compressed about the bone screw by nuts threaded onto a threaded spinal rod. In another approach taken by Harms et al., in U.S. Pat. No. 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al., patents is that the spinal rod must be threaded in order to accept the compression nuts. It is known that threaded rods can tend to weaken the rods in the face of severe spinal loads. Moreover, the design of the bone screws in the '458 and '678 Patents require a multiplicity of parts and are fairly complicated to achieve complete fixation of the bone screw.

A third approach is shown in U.S. Pat. No. 5,304,179 to Wagner, which shows a bone screw fixed inside a bushing and angled with respect to the longitudinal axis of the bushing. The bushing is rotatable within a portion of a connector angled with respect to the axis of the adjoining instrumentation. The connector is rotatable around the instrumentation axis. One detriment of the Wagner system is that only discrete positions of a bone screw in three-dimensional space can be achieved. Further, the Wagner system also requires threaded spinal rods and a multiplicity of complicated parts with their above-described drawbacks.

There is therefore a need remaining in the art for a multi-axial bone engaging fastener that can be readily and securely engaged to an elongated member, such as a spinal rod, of any configuration—i.e., smooth, roughened, knurled or threaded. There is also a need for such a multi-axial bone engaging fastener which minimizes the profile and bulk of the components used to engage a bone fastener, such as a bone screw, to the spinal rod in its various angular orientations. Further, there is a need for a multi-axial engaging fastener which allows the positioning of the fastener at a continuous range of spatial angles between the fastener and an axis perpendicular to the elongated member.

SUMMARY OF THE INVENTION

In one embodiment of the invention, a spinal fixation assembly is provided that includes a bone engaging fastener, such as a bone screw, and an elongated member, such as a spinal rod. The fixation assembly includes a multi-axial assembly that permits fixation of the bone screw to the spinal rod at any of a plurality of angles relative to the rod in three-dimensional space. In one aspect of the invention, a bone screw is included having a head with a tool-engaging recess defined therein and a shank portion. In one embodiment, the bone screw includes a circumferential bead between the head and the shank portion of the bone screw. In another embodiment, the bone screw includes a tapered shank portion below the head.

The multi-axial assembly also includes a receiver member having a bore therethrough from a top end to a bottom end. The walls defining the bore are tapered near the bottom or distal end of the receiver member. The receiver member also includes a channel communicating with the bore and having an upper opening at the top of the receiver member for insertion of the elongated member.

In a further aspect of the invention, the multi-axial assembly includes an outer wedge member having a tapered outside surface and which is insertable into the bore of the receiver member to self-lock with the tapered wall of the bore. The outer wedge member includes a bore therethrough which is inclined with respect to the central axis of the outer wedge member. In one aspect, the inclined bore can be inwardly tapered from the top to the middle of the outer wedge member, and then sloped outward to an opening at the bottom of the outer wedge member.

The multi-axial assembly additionally includes an inner wedge member having a tapered outside surface and which is insertable into the inclined bore of the outer wedge member to self-lock with the tapered wall of the inclined bore. The inner wedge member also includes a bore therethrough which is inclined with respect to the central axis of the inner wedge member. In one embodiment, the bore in the inner wedge member is cylindrical and a groove is included in the wall defining the bore for mating with a circumferential bead of the bone screw. In another embodiment, the bore in the inner wedge member is tapered to self-lock with a tapered shank portion of the bone screw.

The present invention provides an assembly that enables a bone engaging fastener to be fixed to an elongated member at a continuous range of angular orientations relative to the elongated member. In one aspect of the invention, the bone engaging fastener, wedge members, and elongated member are "top loaded" by insertion into the top or proximal opening in the receiver member. When the desired orientation of the fastener is achieved, the fastener can be fixed through self-locking of the bone fastener within the inner wedge member, of the inner wedge member within the outer wedge member, and of the outer wedge member within the receiver member. Self-locking can occur as the fastener is engaged in a bone, as for example when a bone screw is threaded into a bone and tightened. Alternatively, self-locking can occur as the assembly is attached to an elongated member, as for example when a spinal rod presses down on the fastener.

The preferred embodiment of the multi-axial bone fixation assembly provides the advantage of a solid fixation between a spinal rod and a bone engaging fastener regardless of the three-dimensional angle between the two components. A further benefit of the present invention is the minimum number of components necessary to achieve this solid fixation. Another benefit resides in the self-locking capabilities of the wedge members and the receiver member. Other benefits and certain objects of the invention will become apparent upon consideration of the following written description and accompanying figures illustrating one embodiment of the invention.

DESCRIPTION OF THE FIGURES

FIG. 1 is a side elevational view of a multi-axial bone fixation assembly in accordance with one embodiment of the present invention.

FIG. 2 is a cross-sectional view of a multi-axial bone fixation assembly as depicted in FIG. 1.

FIG. 6b is a side elevational view of the outer wedge member as depicted in FIG. 6a.

FIG. 7 is a cross-sectional view along the lines 7—7 and viewed in the direction of the arrows of the outer wedge member as depicted in FIG. 6a.

FIG. 8b is a side elevational view of the inner wedge member as depicted in FIG. 8a.

FIG. 9 is a cross-sectional view along the lines 9—9 and viewed in the direction of the arrows of the inner wedge member as depicted in FIG. 8a.

FIG. 12b is a cross-sectional view of the embodiment of the inner wedge member depicted in FIG. 12a.

FIG. 13b is a cross-sectional view of the embodiment of the outer wedge member depicted in FIG. 13a.

DESCRIPTION OF THE PREFERRED EMBODIMENTS

Figure 3:
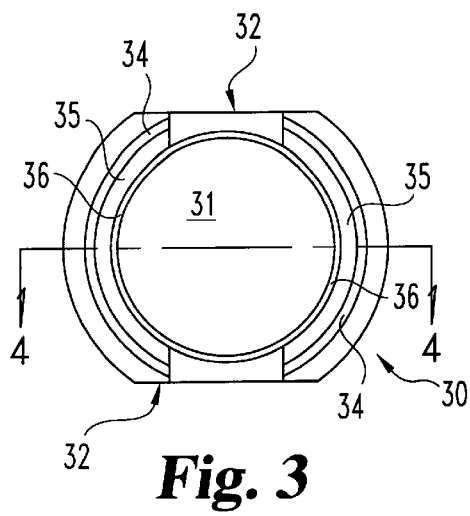
FIG. 3 is a top view of the receiver member of the bone fixation assembly shown in FIGS. 1 and 2.

For the purpose of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

Referring generally to FIGS. 1 and 2, the components of a multi-axial bone fixation assembly 10 in accordance with a preferred embodiment of the present invention are shown. The multi-axial assembly 10 includes a bone screw 20 configured to engage a bone, such as a vertebra. The assembly further includes a receiver member 30 for supporting bone screw 20 and for linking assembly 10 with a spinal rod 80. The assembly further includes an outer wedge member 40 for engagement within the interior of receiver member 30, and an inner wedge member 50 for engagement between bone screw 20 and outer wedge member 40.

Figure 5:
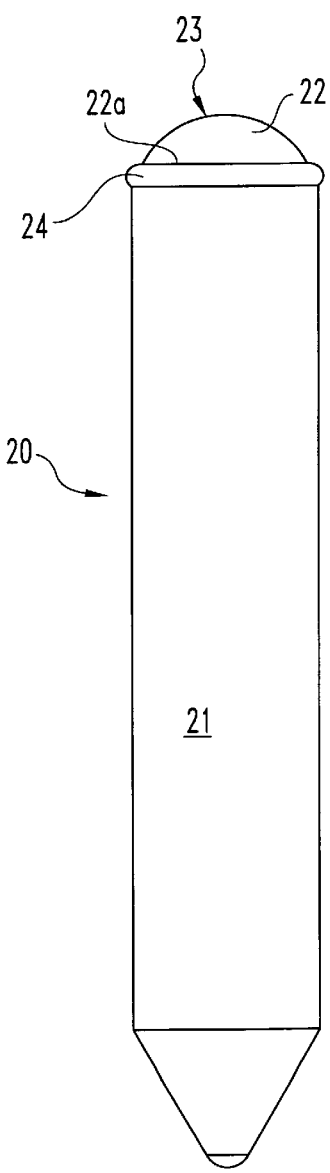
FIG. 5 is a side elevational view of a bone screw for use in the bone fixation assembly shown in FIGS. 1 and 2.

In accordance with one aspect of the invention, bone screw 20 is configured as shown in FIG. 5. Bone screw 20 includes a threaded shank portion 21, a head portion 22, and a circumferential bead 24. Threaded shank portion 21 carries threads configured to anchor the bone screw solidly within a bone. Most preferably, the threads are cancellous threads, or threads readily adapted for solid fixation within the cancellous bone of the vertebral body. It is understood that threaded shank 21 can have a variety of configurations depending on the nature of the bone within which bone screw 20 is engaged. Moreover, the length of threaded shank 21 can be adjusted depending on the anatomy or characteristics of the bone within which bone screw 20 is driven. In one specific embodiment, threaded shank 21 has a length of about 1.5 inches, and is configured with threads for engagement within the pedicle of a lumbar vertebra.

Head portion 22 is located at the upper or proximal end of bone screw 20. Head portion 22 preferably includes a tool receiving slot or recess 20a (see FIG. 2) to accommodate a screw driving tool. In a specific embodiment, head portion 22 is in the shape of a portion of a sphere, and the circumference of the bottom or distal edge 22a of head portion 22 is preferably smaller than the circumference of the threaded shank portion 21. Bead 24 lies between head portion 22 and threaded shank 21. Bead 24 extends circumferentially around the top or proximal end of threaded shank 21 and engages inner wedge member 50 in a manner to be described hereinafter. In one specific embodiment, head 22 is a portion of a sphere of about 0.295 inches in diameter, bead 24 has a width of about 0.040 inches and a diameter of about 0.311 inches, and threaded shank 21 has a length of about 1.534 inches and a diameter of about 0.295 inches.

Figure 4:
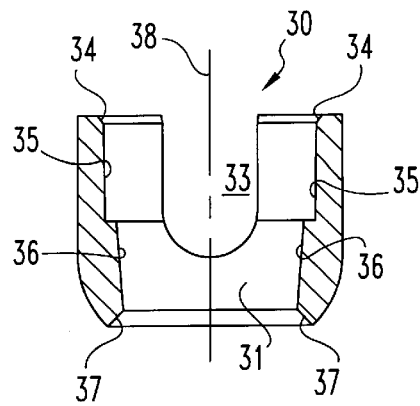
FIG. 4 is a cross-sectional view along the lines 4—4 and viewed in the direction of the arrows of the receiver member as depicted in FIG. 3.

Referring now to FIGS. 3 and 4, bone screw assembly 10 includes a receiver member 30. Receiver member 30, in a preferred embodiment, is generally cylindrical, having a bore 31 therethrough and two opposed truncated side walls 32. Bore 31 and receiver member 30 define a common central longitudinal axis 38. The side walls 32 of receiver member 30 define a channel 33 for receiving spinal rod 80 which extends across receiving member 30, communicating generally perpendicularly with bore 31. Channel 33 may extend to a sufficient depth within receiver member 30 that spinal rod 80 may contact head portion 22 of bone screw 20 in the finished assembly 10, as further described hereinafter.

The inside of receiver member 30 includes a series of surfaces. Entry surface 34 is angled toward axis 38 to facilitate placement of other parts of bone screw assembly 10 therein, as hereinafter further described. Upper inner surface 35 may be substantially parallel to the outer surface of receiver member 30 and may, for example, be internally threaded to accommodate the plug member of the CD® System noted above and shown in FIG. 3. Lower inner surface 36 is angled toward axis 38, thereby forming a self-locking taper for holding outer wedge member 40 as hereinafter further described. Exit surface 37 is angled outward from axis 38 to provide greater range of axial movement for bone screw 20 in the completed bone fixation assembly 10. In the preferred embodiment, channel 33 intersects both the upper and lower inner surfaces 35, 36. In a specific embodiment, lower inner surface 36 includes a Morse taper, preferably forming a four degree angle with axis 38 of receiver member 30, and exit surface 37 comprises a 45 degree angle with axis 38 of receiver member 30.

Figure 6B:
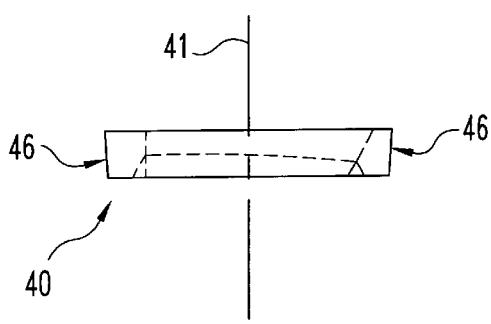
Figure 6A:
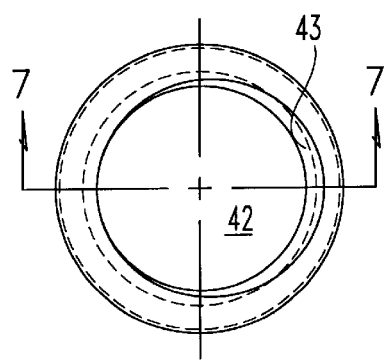
FIG. 6a is a top view of the outer wedge member of the bone fixation assembly of FIGS. 1 and 2.
Figure 7:
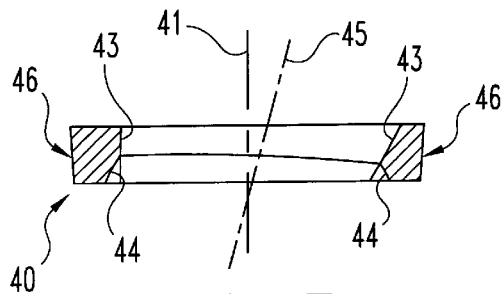

Referring now to FIGS. 6a, 6b and 7, there is shown an outer wedge member 40 according to a preferred embodiment of the present invention. Outer wedge member 40 is generally in the shape of a washer having a central axis 41, an inclined bore 42, and an outer surface 46. Inclined bore 42 extends through outer wedge member 40 from top to bottom and defines a longitudinal axis 45 which is not parallel to central axis 41. In one specific embodiment, the angle formed by bore axis 45 and central axis 41 is fifteen degrees. The surfaces defining bore 42 include an upper tapered wall 43 and a lower wall 44. Upper tapered wall 43 is tapered toward bore axis 45, thereby forming a self-locking taper for holding lower wedge member 50 in a manner described hereafter. In one specific embodiment, upper tapered wall 43 forms an angle of four degrees with bore axis 45. In a second and third specific embodiment, upper tapered wall 43 forms an angle of fifteen and thirty degrees, respectively, with bore axis 45. Lower wall 44 is generally conical, flaring outward toward the bottom of outer wedge member 40 to allow greater range of axial movement for bone screw 20 in the completed bone fixation assembly 10. Tapered outer surface 46 is angled from top to bottom toward central axis 41 of outer wedge member 40. In a specific embodiment, tapered outer surface 46 includes a Morse taper, forming an angle of four degrees with central axis 41. Tapered outer surface 46 self locks with tapered inner surface 36 of receiver member 30 in a manner to be described hereafter.

Figure 8B:
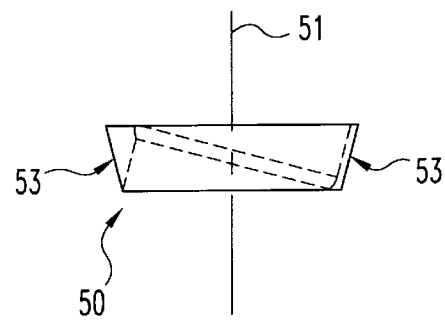
Figure 8A:
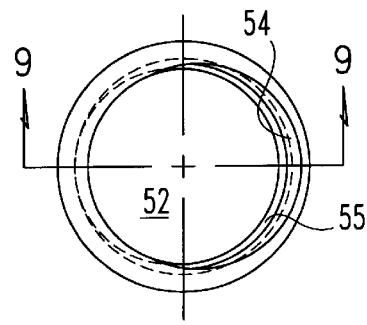
FIG. 8a is a top view of the inner wedge member of the bone fixation assembly shown in FIGS. 1 and 2.
Figure 9:
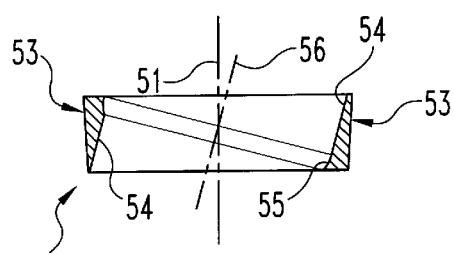

Referring now to FIGS. 8a, 8b and 9, an inner wedge member 50 according to a preferred embodiment of the present invention is shown. Inner wedge member 50 is generally in the shape of a washer having a central axis 51, an inclined bore 52, and an outer surface 53. Inclined bore 52 extends through inner wedge member 50 top to bottom and defines a longitudinal axis 56 which is not parallel to central axis 51. Bore 52 is defined by generally cylindrical inner surface 54. In one specific embodiment, the angle formed by bore axis 56 and central axis 51 is fifteen degrees. Inner surface 54 has an inner diameter slightly greater than the outer diameter of circumferential bead 24. Inner surface 54 also includes inner circumferential groove 55. Groove 55 is shaped to mate with circumferential bead 24 of bone screw 20 and is thereby a means for holding bone screw 20. Outer surface 53 of inner wedge member 50 is tapered with respect to central axis 51. In one specific embodiment, the angle between outer surface 53 and central axis 51 is four degrees. In a second and third specific embodiment, outer surface 53 and central axis 51 form angles of fifteen and thirty degrees, respectively.

In use, outer wee member 40 is inserted into bore 31 of receiver member 30 through the top or proximal end of receiver member 30. Tapered outer surface 46 of outer wedge member 40 fits within tapered lower inner surface 36 of receiver member 30. Outer wedge member 40 is rotatable within bore 31 until finally seated and tightened. Inner wedge member 50 is inserted into bore 42 of outer wedge member 40. Tapered outer surface 53 of inner wedge member 50 fits within tapered upper wall 43 of bore 42 of outer wedge member 40. Inner wedge member 50 is rotatable within bore 42 until finally seated and tightened. Bone screw 20 is inserted into bore 52 of inner wedge member 50, with circumferential bead 24 of bone screw 20 fitted into groove 55. Bone screw 20 is then preferably threaded at least partially into the bone.

After the components are in place, the surgeon may realize any of a continuous range of three-dimensional angular orientations of bone screw 20 with respect to axis 38 (and thereby with respect to a spinal rod within channel 33) by rotating wedge members 40 and/or 50, with respect to each other and/or with respect to receiver member 30. The surgeon can manipulate the receiver member 30 with respect to the bone screw to align channel 33 with a spinal rod already in place or to be placed when a plurality of assemblies 10 are implanted. As noted, in one specific embodiment the angle between central axis 41 and bore axis 45 of outer wedge member 40 and the angle between central axis 51 and bore axis 56 of inner wedge member 50 are each fifteen degrees. In that embodiment, bone screw 20 can assume any position which forms an angle of zero to thirty degrees between bone screw 20 and axis 38 of receiver member 30.

When the desired angle and position of bone screw 20 is achieved, a pushing force on head 22 and/or a pulling force on shank 21 and/or receiver member 30 is applied to seat and tighten bone screw 20 and inner wedge member 50 in outer wedge member 40 and outer wedge member 40 in receiver member 30. In one embodiment, a pushing force is provided by a spinal rod 80 which is inserted into channel 33 to contact head 22 of bone screw 20. A retaining means 70, such as a threaded nut or plug, is used to retain the spinal rod in contact with head 22. Alternatively or additionally, in this instance head 22 or spinal rod 80 or both may include additional feature(s) to enhance fixation. Though spinal rod 80 and head 22 contact nominally at a single point, the wedge members 40, 50 are solidly locked thereby.

A pulling force can be provided by further tightening of bone screw 20 into the bone. In this instance, receiver member 30 will contact the bone as well to provide a reactive force as bone screw 20 is tightened. Further, in this example contact between spinal rod 80 and head 22 of bone screw 20 is unnecessary.

Figure 10:
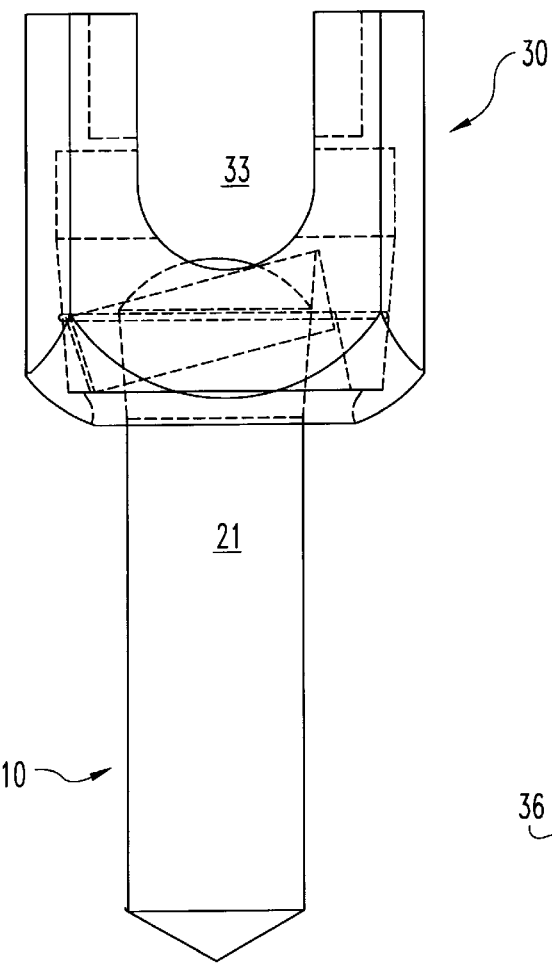
FIG. 10 is a side elevational view of a multi-axial bone fixation assembly in accordance with an additional embodiment of the present invention.
Figure 11:
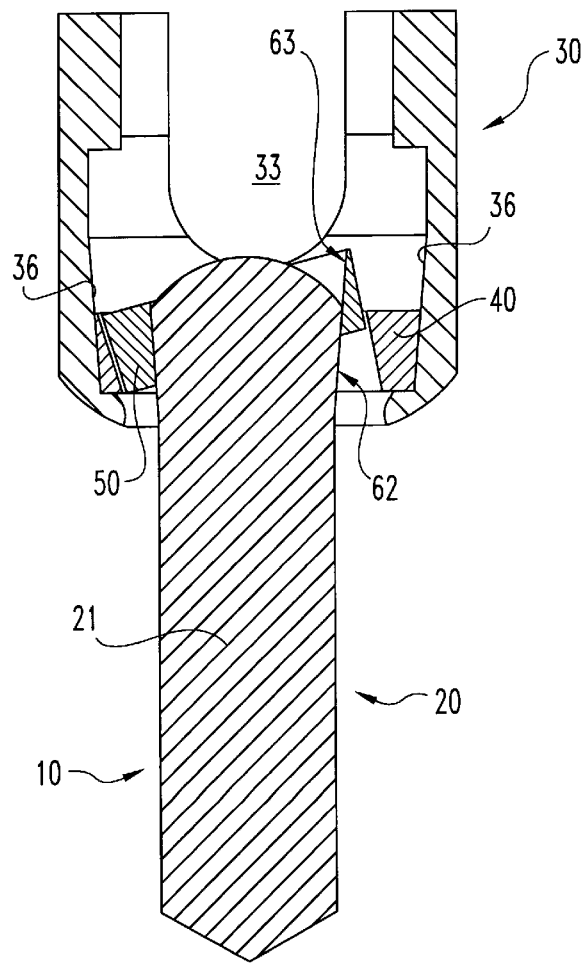
FIG. 11 is a cross-sectional view of the multi-axial bone fixation assembly as depicted in FIG. 10.
Figure 12A:
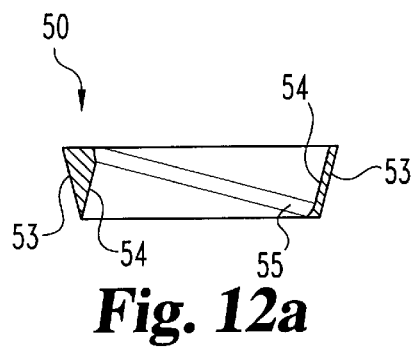
FIG. 12a is a side elevational view of a second embodiment of the inner wedge member of the present invention.
Figure 13A:
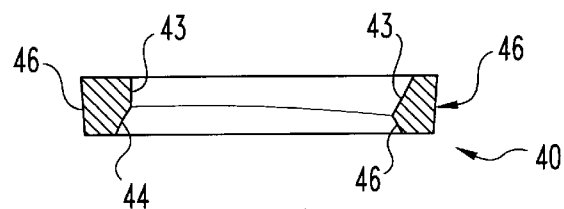
FIG. 13a is a side elevational view of a second embodiment of the outer wedge member of the present invention.
Figure 12B:
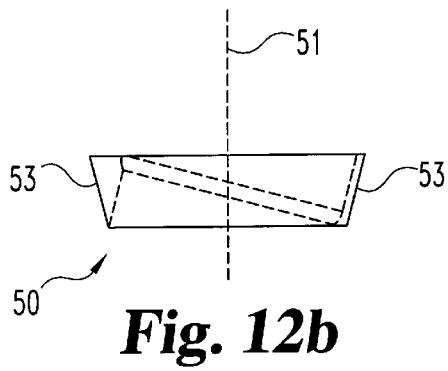
Figure 13B:
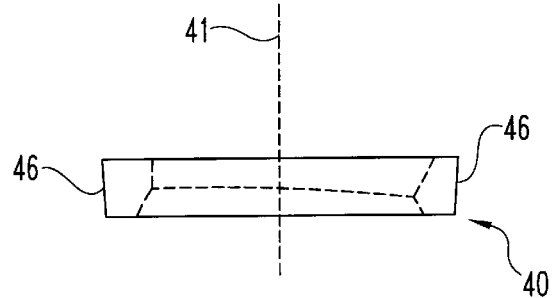
Figure 14:
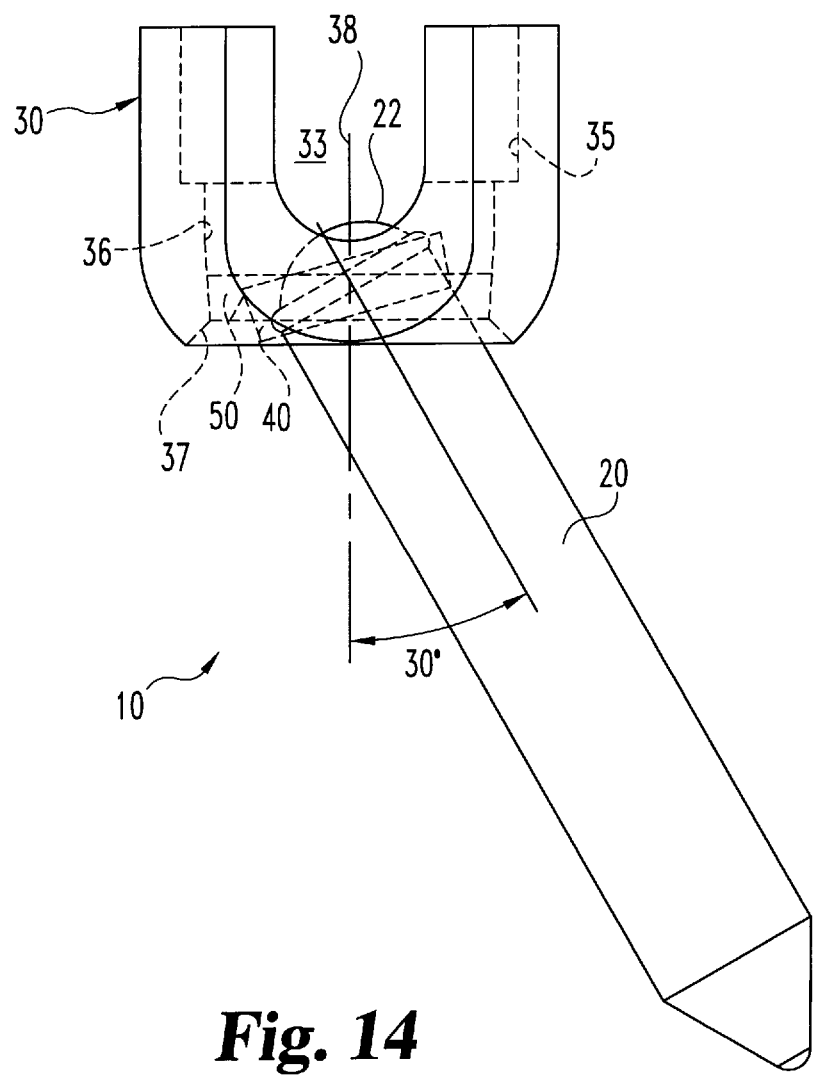
FIG. 14 is a side elevational view of the bone fixation assembly of the present invention in which the bone screw is oriented at an angle with respect to a central axis of the receiver member of the present invention.

An alternative embodiment of the invention is shown in FIGS. 10 and 11. In FIG. 10, bone screw 20 includes head 61 and a shank portion 62 having a self-locking taper. Additionally, inner surface 63 of inner wedge member 50 is tapered. Bone screw 20 is inserted into inner wedge member 50, and friction fit is achieved between tapered shank portion 62 and inner surface 63, with inner surface 63 forming a means for holding bone screw 20. In this alternative embodiment, bone screw 20 having shank 62, inner wedge member 50 having inner surface 63, outer wedge member 40, and receiver member 30 are assembled in the manner already described. Varying spatial angles of bone screw 20 with respect to axis 38 are realized by rotation of bone screw 20, inner wedge member 50, and/or outer wedge member 40 within receiver member 30 in the manner already described.

The above-disclosed components of the present invention are preferably comprised of a biocompatible material such as stainless steel, titanium, or other material suitable for in vivo implantation.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone fixation assembly for engaging an elongated member comprising:

a receiver member defining a channel for receiving an elongated member, said receiver member having a bore therethrough defining an inner surface;

a first wedge member for complementary mating within said inner surface of said receiver member, said first wedge member defining a first central axis, said first wedge member further defining a bore therethrough which is inclined with respect to said first central axis;

a second wedge member for complementary mating within said bore of said first wedge member, said second wedge member defining a second central axis, said second wedge member further defining a bore therethrough which is inclined with respect to said second central axis; and a bone engaging fastener for complementary mating within said bore of said second wedge member.

2. The bone fixation assembly of claim 1 wherein:

said bone engaging fastener includes a circumferential bead; and said bore of said second wedge member communicates with a circumferential groove for mating with said circumferential bead.

3. The bone fixation assembly of claim 1 wherein:

said bone engaging fastener includes a tapered shank portion; and said bore of said second wedge member being tapered to allow said tapered shank portion of said bone engaging fastener to tightly fit within said bore of said second wedge member.

4. The bone fixation assembly of claim 1 wherein an angle formed by said bore of said first wedge member and said first central axis and an angle formed by said bore of said second wedge member and said second central axis are equal.

5. The bone fixation assembly of claim 4 wherein said angles measure about fifteen degrees.

6. The bone fixation assembly of claim 1 wherein said bone engaging fastener is a bone screw.

7. The bone fixation assembly of claim 6 wherein:

said bone screw includes a circumferential bead; and said bore of said second wedge member communicates with a circumferential groove for mating with said circumferential bead.

8. The bone fixation assembly of claim 6 wherein:

said bone screw includes a tapered shank portion; and said bore of said second wedge member being tapered to allow said tapered shank portion of said bone screw to tightly fit within said bore of said second wedge member.

9. The bone fixation assembly of claim 6 wherein an angle formed by said bore of said first wedge member and said first central axis and an angle formed by said bore of said second wedge member and said second central axis are equal.

10. The bone fixation assembly of claim 9 wherein said angles measure about fifteen degrees.

11. A bone fixation assembly for engagement to an elongated member comprising:

a bone engaging fastener;

a receiver member defining a channel for receiving an elongated member, said receiver member having a bore therethrough defining an inner surface, said inner surface having at least a portion which is inwardly tapered;

a first wedge member defining a first central axis, said first wedge member further defining a bore therethrough, said bore being inclined with respect to said first central axis and tapered, and said first wedge member further having an outer surface which is tapered for complementary mating with said tapered portion of said inner surface of said receiver member; and a second wedge member defining a second central axis, said second wedge member further defining bore therethrough, said bore being inclined with respect to said second central axis, and said second wedge member further having an outer surface which is tapered for complementary fitting within said bore of said first wedge member, wherein said inner s fsaid second wedge member includes means for holding said bone engaging fastener.

12. The bone fixation assembly of claim 11 wherein:

said bone engaging fastener includes a circumferential bead; and said means for holding includes a groove for mating with said circumferential bead.

13. The bone fixation assembly of claim 11 wherein:

said bone engaging fastener includes a tapered shank portion; and said means for holding includes a at least a portion of said inner surface of said second wedge member, said portion being tapered for fitting with said tapered shank portion of said bone engaging fastener.

14. The bone fixation assembly of claim 11 wherein the angle formed by said bore of said first wedge member and said first central axis and the angle formed by said bore of said second wedge member and said second central axis are equal.

15. The bone fixation assembly of claim 14 wherein said angles measure about fifteen degrees.

16. The bone fixation assembly of claim 11 wherein said bone engaging fastener is a bone screw.

17. The bone fixation assembly of claim 16 wherein:

said bone engaging fastener includes a circumferential bead; and said means for holding includes a groove for mating with said circumferential bead.

18. The bone fixation assembly of claim 16 wherein:

said bone engaging fastener includes a tapered shank portion; and said means for holding includes a at least a portion of said inner surface of said second wedge member, said portion being tapered for fitting with said tapered shank portion of said bone engaging fastener.

19. The bone fixation assembly of claim 16 wherein an angle formed by said bore of said first wedge member and said first central axis and an angle formed by said bore of said second wedge member and said second central axis are equal.

20. The bone fixation assembly of claim 19 wherein said angles measure about fifteen degrees.

21. A bone screw assembly comprising:

a bone screw having a head portion, a shank portion, and a circumferential bead therebetween;

a receiver member for receiving an elongated member, said receiver member having a bore therethrough defining an inner surface, said inner surface having at least a part which is inwardly tapered;

a first wedge member having a first central longitudinal axis, said first wedge member further having a bore therethrough, said bore being inclined at an angle of about fifteen degrees to said first central longitudinal axis, said bore further defining tapered walls, and said first wedge member further having a tapered outer surface for fitting with said tapered part of said inner surface of said receiver member; and a second wedge member having a second central longitudinal axis, said second wedge member further having a bore therethrough, said bore being inclined at an angle of about fifteen degrees to said second central longitudinal axis, said bore further defining an inner surface, said inner surface of said second wedge member having a groove for receiving said circumferential bead said second wedge member further having a tapered outer surface for fitting with said tapered walls of said bore of said first wedge member.

* * * * *